US011648059B2

(12) United States Patent
Culman et al.

(10) Patent No.: US 11,648,059 B2
(45) Date of Patent: May 16, 2023

(54) ENHANCING VISIBLE DIFFERENCES BETWEEN DIFFERENT TISSUES IN COMPUTER-ASSISTED TELE-OPERATED SURGERY

(71) Applicant: Intuitive Surgical Operations, Inc., Sunnyvale, CA (US)

(72) Inventors: William Jason Culman, Sunnyvale, CA (US); Jeffrey M. DiCarlo, Austin, TX (US); Ian E. McDowall, Woodside, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 350 days.

(21) Appl. No.: 16/649,111

(22) PCT Filed: Sep. 21, 2018

(86) PCT No.: PCT/US2018/052230
§ 371 (c)(1),
(2) Date: Mar. 19, 2020

(87) PCT Pub. No.: WO2019/060733
PCT Pub. Date: Mar. 28, 2019

(65) Prior Publication Data
US 2020/0289203 A1 Sep. 17, 2020

Related U.S. Application Data

(60) Provisional application No. 62/561,814, filed on Sep. 22, 2017.

(51) Int. Cl.
*A61B 34/10* (2016.01)
*A61B 34/37* (2016.01)
(Continued)

(52) U.S. Cl.
CPC .............. *A61B 34/10* (2016.02); *A61B 34/35* (2016.02); *A61B 34/37* (2016.02); *A61B 90/37* (2016.02);
(Continued)

(58) Field of Classification Search
CPC ....................................................... A61B 34/10
(Continued)

(56) References Cited

U.S. PATENT DOCUMENTS 8,320,996 B2 * 11/2012 Panasyuk ............... G01N 21/21
600/407
8,374,682 B2 * 2/2013 Freeman ................. A61B 5/444
600/476

(Continued)

FOREIGN PATENT DOCUMENTS

CN 105899143 A 8/2016
JP H0973461 A 3/1997
(Continued)

OTHER PUBLICATIONS

International Search Report and Written Opinion in related International Application No. PCT/US2018/052230, dated Apr. 12, 2019, 10 pages.

(Continued)

*Primary Examiner* — Javid A Amini
(74) *Attorney, Agent, or Firm* — Fish & Richardson P.C.

(57) ABSTRACT

The technology described herein can be embodied in a method that includes obtaining a representation of a first image of a surgical scene using electromagnetic radiation of a first wavelength range outside the visible range of wavelengths, wherein an amount of electromagnetic radiation of the first wavelength range received from a first tissue type is lower than that received for a second tissue type. The method also includes obtaining a representation of a second
(Continued)

image using electromagnetic radiation of a second wavelength range outside the visible range of wavelengths, wherein an amount of electromagnetic radiation of the second wavelength range received from the second tissue type is substantially different from that received for the first tissue type. The visual representation of the surgical scene is rendered on the one or more displays using the representation of the first image and the representation of the second image.

20 Claims, 5 Drawing Sheets

(51) Int. Cl.
*A61B 34/35* (2016.01)
*A61B 90/00* (2016.01)

(52) U.S. Cl.
CPC ... *A61B 2034/105* (2016.02); *A61B 2090/373* (2016.02)

(58) Field of Classification Search
USPC .......................................................... 703/11
See application file for complete search history.

(56) References Cited

U.S. PATENT DOCUMENTS

| | | | | |
|---|---|---|---|---|
| 8,644,911 B1* | 2/2014 | Panasyuk | ................. | G01J 3/28 600/476 |
| 2008/0051664 A1* | 2/2008 | Demos | ................... | A61B 1/063 600/473 |
| 2015/0141847 A1* | 5/2015 | Sarvazyan | ............. | A61B 90/37 600/478 |
| 2015/0366455 A1* | 12/2015 | Bezemer | .............. | A61B 5/0082 600/476 |
| 2016/0364858 A1* | 12/2016 | Butte | ........................ | G01J 1/44 |

FOREIGN PATENT DOCUMENTS

| | | | | |
|---|---|---|---|---|
| JP | 2013063259 A | 4/2013 | | |
| JP | 2017500550 A | 1/2017 | | |
| KR | 100952853 B1 | 4/2010 | | |
| WO | WO-2014139020 A1 | 9/2014 | | |
| WO | WO-2015142800 A1 | 9/2015 | | |
| WO | WO-2016100214 A1 | 6/2016 | | |
| WO | WO-2016154589 A1 * | 9/2016 | ........... | A61B 1/0005 |

OTHER PUBLICATIONS

Extended European Search Report for Application No. EP18858318.1 dated Mar. 22, 2021, 09 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

ENHANCING VISIBLE DIFFERENCES BETWEEN DIFFERENT TISSUES IN COMPUTER-ASSISTED TELE-OPERATED SURGERY

CROSS-REFERENCE TO RELATED APPLICATION

This application is a U.S. National Stage Application under 35 USC § 371 and claims the benefit of International Patent Application No. PCT/US2018/052230 filed on Sep. 21, 2018, which claims priority to U.S. Provisional Application Ser. No. 62/561,814, filed Sep. 22, 2017, the disclosure of each of which is hereby incorporated by reference in its entirety.

TECHNICAL FIELD

This disclosure relates to devices and methods for minimally invasive computer-assisted tele-operated surgery.

BACKGROUND

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. The surgeon performs the surgical procedures on the patient by manipulating master control input devices, which in turn control the motion of robotic instruments.

SUMMARY

In one aspect, this document features a method of providing visual feedback during a surgical process using a visual representation of a surgical scene rendered on one or more displays associated with a surgical device. The method includes obtaining a representation of a first image of the surgical scene using electromagnetic radiation of a first wavelength range that lies outside the visible range of wavelengths, wherein an amount of electromagnetic radiation of the first wavelength range received by one or more sensors from a first tissue type is lower than an amount of electromagnetic radiation of the first wavelength range received for a second tissue type. The method also includes obtaining a representation of a second image of the surgical scene using electromagnetic radiation of a second wavelength range that lies outside the visible range of wavelengths, wherein an amount of electromagnetic radiation of the second wavelength range received by the one or more sensors from the second tissue type is substantially different than an amount of electromagnetic radiation of the second wavelength range received for the first tissue type. The method further includes presenting the visual representation of the surgical scene on the one or more displays, wherein the visual representation is rendered using the representation of the first image and the representation of the second image.

In another aspect, this document features a method of providing visual feedback during a surgical process using a visual representation of a surgical scene rendered on one or more displays associated with a surgical device. The method includes obtaining a representation of a first image of the surgical scene using electromagnetic radiation of a first wavelength range that lies outside the visible range of wavelengths, wherein an amount of electromagnetic radiation of the first wavelength range received by one or more image sensors from a first tissue type is lower than an amount of electromagnetic radiation of the first wavelength range received for a second tissue type. The method also includes obtaining a representation of a second image of the surgical scene using electromagnetic radiation of a second wavelength range that lies outside the visible range of wavelengths, wherein an amount of electromagnetic radiation of the second wavelength range received by the one or more image sensors from a first tissue type is greater than an amount of electromagnetic radiation of the first wavelength range received for a second tissue type. The method further includes obtaining a representation of a third image of the surgical scene using substantially white light illumination, and presenting the visual representation of the surgical scene on the one or more displays, wherein the visual representation is rendered using the representation of the first and second images in combination with the representation of the third image.

In another aspect, this document features a method of providing visual feedback during a surgical process using a visual representation of a surgical scene rendered on one or more displays associated with a surgical device. The method includes obtaining a representation of a first image of the surgical scene using electromagnetic radiation of a first wavelength range that lies outside the visible range of wavelengths, wherein an amount of electromagnetic radiation of the first wavelength range received by one or more image sensors from a first tissue type is lower than an amount of electromagnetic radiation of the first wavelength range received for a second tissue type. The method also includes obtaining a representation of a second image of the surgical scene using electromagnetic radiation of a second wavelength range that lies outside the visible range of wavelengths, wherein an amount of electromagnetic radiation of the second wavelength range received by the one or more image sensors from a first tissue type is greater than an amount of electromagnetic radiation of the first wavelength range received for a second tissue type. The method further includes obtaining a representation of a third image of the surgical scene using substantially white light illumination, and presenting the visual representation of the surgical scene on the one or more displays, wherein the visual representation is rendered using the representation of the first and second images in combination with the representation of the third image.

In another aspect, this document features a surgical system that includes one or more display devices, one or more sensors configured to receive electromagnetic radiation reflected or transmitted from a surgical scene, and one or more processing devices. The one or more processing devices are configured to obtain a representation of a first image of a surgical scene using electromagnetic radiation of a first wavelength range that lies outside the visible range of wavelengths, wherein an amount of electromagnetic radiation of the first wavelength range received by the one or more image sensors from a first tissue type is lower than an amount of electromagnetic radiation of the first wavelength range received for a second tissue type. The processing devices are also configured to obtain a representation of a second image of the surgical scene using electromagnetic radiation of a second wavelength range that lies outside the visible range of wavelengths, wherein an amount of electromagnetic radiation of the second wavelength range received by the one or more image sensors from the second tissue type is substantially different from an amount of electromagnetic radiation of the second wavelength range received for the first tissue type. The processing devices are further configured to present a visual representation of the surgical scene on the one or more displays, wherein the visual representation is rendered using the representation of the first image and the representation of the second image.

In another aspect, this document features a surgical system that includes one or more display devices, one or more image sensors configured to receive electromagnetic radiation reflected or transmitted from a surgical scene, and one or more processing devices. The one or more processing devices are configured to obtain a representation of a first image of a surgical scene using electromagnetic radiation of a first wavelength range that lies outside the visible range of wavelengths, wherein an amount of electromagnetic radiation of the first wavelength range received by the one or more image sensors from a first tissue type is lower than an amount of electromagnetic radiation of the first wavelength range received for a second tissue type. The processing devices are also configured to obtain a representation of a second image of the surgical scene using substantially white light illumination, and present the visual representation of the surgical scene on the one or more displays, wherein the visual representation is rendered using the representation of the first image in combination with the representation of the second image.

In another aspect, this document features a surgical system that includes one or more display devices, one or more image sensors configured to receive electromagnetic radiation reflected or transmitted from a surgical scene, and one or more processing devices. The one or more processing devices are configured to obtain a representation of a first image of the surgical scene using electromagnetic radiation of a first wavelength range that lies outside the visible range of wavelengths, wherein an amount of electromagnetic radiation of the first wavelength range received by one or more image sensors from a first tissue type is lower than an amount of electromagnetic radiation of the first wavelength range received for a second tissue type. The processing devices are also configured to obtain a representation of a second image of the surgical scene using electromagnetic radiation of a second wavelength range that lies outside the visible range of wavelengths, wherein an amount of electromagnetic radiation of the second wavelength range received by the one or more image sensors from a first tissue type is greater than an amount of electromagnetic radiation of the first wavelength range received for a second tissue type. The processing devices are further configured to obtain a representation of a third image of the surgical scene using substantially white light illumination, and present the visual representation of the surgical scene on the one or more displays, wherein the visual representation is rendered using the representation of the first and second images in combination with the representation of the third image.

In another aspect, this document features one or more machine-readable non-transitory storage devices encoded with machine-readable instructions configured to cause one or more processing devices to perform various operations. The operations include obtaining a representation of a first image of the surgical scene using electromagnetic radiation of a first wavelength range that lies outside the visible range of wavelengths, wherein an amount of electromagnetic radiation of the first wavelength range received by one or more image sensors from a first tissue type is lower than an amount of electromagnetic radiation of the first wavelength range received for a second tissue type. The operations further include obtaining a representation of a second image of the surgical scene using electromagnetic radiation of a second wavelength range that lies outside the visible range of wavelengths, wherein an amount of electromagnetic radiation of the second wavelength range received by the one or more image sensors from the second tissue type is substantially different than an amount of electromagnetic radiation of the second wavelength range received for the first tissue type. The operations also include presenting the visual representation of the surgical scene on the one or more displays, wherein the visual representation is rendered using the representation of the first image and the representation of the second image.

In another aspect, this document features one or more machine-readable non-transitory storage devices encoded with machine-readable instructions configured to cause one or more processing devices to perform various operations that include obtaining a representation of a first image of the surgical scene using electromagnetic radiation of a first wavelength range that lies outside the visible range of wavelengths, wherein an amount of electromagnetic radiation of the first wavelength range received by an image sensor from a first tissue type is lower than an amount of electromagnetic radiation of the first wavelength range received for a second tissue type. The operations also include obtaining a representation of a second image of the surgical scene using substantially white light illumination, and presenting the visual representation of the surgical scene on the one or more displays, wherein the visual representation is rendered using the representation of the first image in combination with the representation of the second image.

In another aspect, this document features one or more machine-readable non-transitory storage devices encoded with machine-readable instructions configured to cause one or more processing devices to perform various operations that include obtaining a representation of a first image of the surgical scene using electromagnetic radiation of a first wavelength range that lies outside the visible range of wavelengths, wherein an amount of electromagnetic radiation of the first wavelength range received by one or more image sensors from a first tissue type is lower than an amount of electromagnetic radiation of the first wavelength range received for a second tissue type. The operations also include obtaining a representation of a second image of the surgical scene using electromagnetic radiation of a second wavelength range that lies outside the visible range of wavelengths, wherein an amount of electromagnetic radiation of the second wavelength range received by the one or more image sensors from a first tissue type is greater than an amount of electromagnetic radiation of the first wavelength range received for a second tissue type. The operations further include obtaining a representation of a third image of the surgical scene using substantially white light illumination, and presenting the visual representation of the surgical scene on the one or more displays, wherein the visual representation is rendered using the representation of the first and second images in combination with the representation of the third image.

In another aspect, this document features a method of providing visual feedback during a surgical process using a visual representation of a surgical scene rendered on one or more displays associated with a surgical device. The method includes obtaining a representation of an image of the surgical scene using electromagnetic radiation of a wavelength range that lies outside the visible range of wavelengths, wherein an amount of electromagnetic radiation of the wavelength range received by one or more sensors from collagen is lower than an amount of electromagnetic radiation of the wavelength range received for lipid, and presenting the visual representation of the surgical scene on the one or more displays using the representation of the image.

Implementations of the above aspects can include one or more of the following.

An input device can be used to receive user-input for controlling at least a portion of the surgical device, wherein the user-input is received in response to presenting the visual representation. In some implementations, the user-input enables a toggling between the visual representation and a normal surgical view. The first tissue type can be collagen, and the second tissue type can be lipid. The visual representation can include enhanced visible differences between a representation of a ureter and a representation of surrounding lipid layers. Each of the first wavelength range and the second wavelength range can be in the range 700-2000 nm. The first wavelength range can be 1300-1350 nm and the second wavelength range can be 1200-1250 nm.

Obtaining the representation of the first or second image of the surgical scene using electromagnetic radiation of the first or second wavelength range, respectively, can include illuminating the surgical scene using electromagnetic radiation of the first wavelength range or the second wavelength range, and generating the representation of the first image or second image, respectively, using data captured by the one or more sensors, wherein the one or more sensors are configured to sense portions of the electromagnetic radiation reflected or transmitted from the surgical scene. Illuminating the surgical scene using electromagnetic radiation in the first wavelength range or the second wavelength range can include illuminating the surgical scene using electromagnetic radiation in the first wavelength range during a first time period, and illuminating the surgical scene using electromagnetic radiation in the second wavelength range during a second time period that is at least partially non-overlapping with the first time period. Obtaining the representation of the first or second image of the surgical scene using electromagnetic radiation in the first or second wavelength ranges, respectively, can include illuminating the surgical scene using broadband electromagnetic radiation that includes multiple wavelengths, and generating the representation of the first image using data captured by a first sensor configured to sense a first portion of the electromagnetic radiation reflected or transmitted from the surgical scene, wherein the first portion of the electromagnetic radiation passes through a first filter configured to selectively pass electromagnetic radiation in the first wavelength range, and generating the representation of the second image using data captured by the first sensor or a second sensor configured to sense a second portion of the electromagnetic radiation reflected or transmitted from the surgical scene, wherein the second portion of the electromagnetic radiation passes through a second filter configured to selectively pass electromagnetic radiation in the second wavelength range. Obtaining the representation of the first or second image of the surgical scene using electromagnetic radiation in the first or second wavelength ranges, respectively, can include illuminating the surgical scene using broadband electromagnetic radiation that includes multiple wavelengths, generating the representation of the first image using data captured by a first sensor configured to selectively sense a first portion of the electromagnetic radiation in the first wavelength range, as reflected or transmitted from the surgical scene, and generating the representation of the second image using data captured by the first sensor or a second sensor configured to selectively sense a second portion of the electromagnetic radiation in the second wavelength as reflected or transmitted from the surgical scene.

A representation of a third image of the surgical scene can be obtained based on a third wavelength range that lies outside the visible range of wavelengths, and the visual representation of the surgical scene can be presented on the display, wherein the visual representation is rendered also using the representation of the third image. The third wavelength range can be selected such that an absorption of electromagnetic radiation in the third wavelength range for lipid is substantially equal to an absorption of electromagnetic radiation in the third wavelength range for collagen. The third wavelength range can be selected such that an absorption of electromagnetic radiation in the third wavelength for lipid is substantially different from an absorption of electromagnetic radiation in the third wavelength range for collagen. The representation of the first image can be generated in a third wavelength range that lies inside the visible range of wavelengths. The representation of the second image can be generated in a fourth wavelength range that lies inside the visible range of wavelengths, and the representations of the first and second images can be combined to generate the visual representation of the surgical scene.

Some or all of the embodiments described herein may provide one or more of the following advantages. Visible differences between two or more different types of tissues can be enhanced in images presented on a surgeon's display device. In some cases, where the different tissue types are adjacent to one another, this may assist the surgeon to access only the desired tissues, thereby potentially improving the accuracy of the surgical process. For example, by judicious selection of imaging wavelengths that enhance the differences between collagen and lipid, the technology described herein may allow for improved visualization of the urethra (which consists primarily of collagen) in the presence of surrounding layers of lipids. This in turn may assist some surgeons, in particular less experienced surgeons, to perform surgeries on a telesurgery system with increased confidence.

BRIEF DESCRIPTION OF THE DRAWINGS

FIG. 10 is a side view of an example robotic manipulator arm assembly of a computer-assisted tele-operated surgery system.

DETAILED DESCRIPTION

Figure 1B:
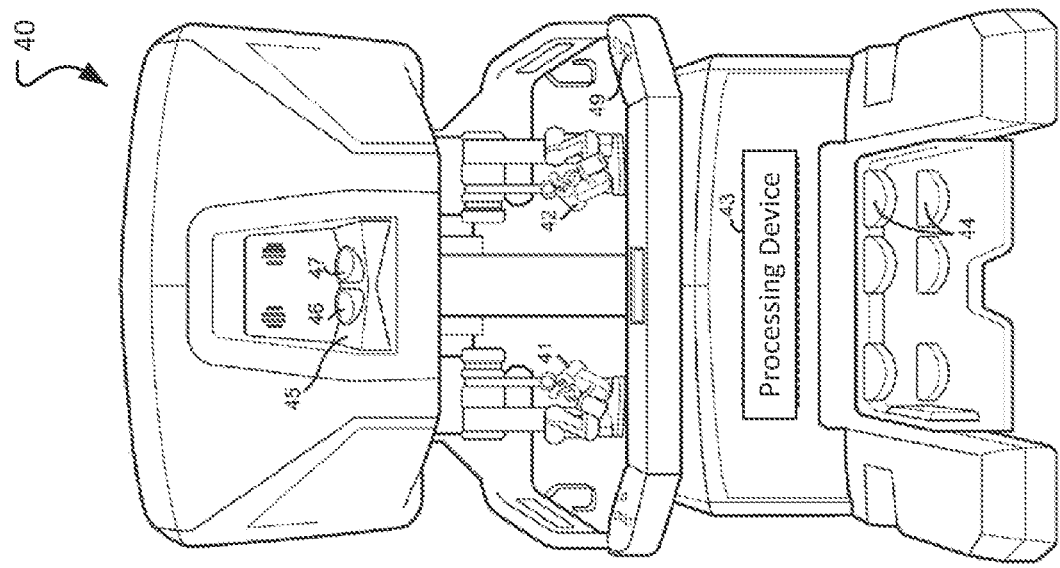
FIG. 1B is a front view of an example surgeon console of a computer-assisted tele-operated surgery system.

This document describes technology that, in some cases, improves visualization of surgical sites and anatomical parts during image-guided surgical processes such as minimally invasive robotic surgery (also referred to herein as minimally invasive surgery (MIS)). For example, the technology allows for enhancing visible differences between different tissue types at a surgical site, as displayed on a surgeon's console. In some cases, this in turn may allow for improved visualization of tissues that may otherwise be relatively more indistinguishable in the presence of adjacent tissues of a different kind. For example, a human ureter is typically embedded within layers of fat, and it may be challenging to distinguish the location of the ureter when imaged using wavelengths in the visible range. The technology described herein allows for reduced-band imaging where the imaging wavelengths are selected to enhance visible differences between tissues in the representation rendered on the surgeon's console or display device. In the example of the ureter and fat, the imaging wavelengths can be selected such that the absorption characteristics of collagen (the primary constituent of ureter) versus fat differ for the selected wavelengths resulting in an ability to capture, process, and/or augment an image with an enhancement of visible differences between the ureter and surrounding fat layers in the image rendered on the surgeon's console. In some cases, this may result in the ureter being more distinguishable from the adjacent and covering fat layers, and therefore allow the surgeon to navigate in the surgical site with more confidence because the location of a delicate structure is more salient, as compared to the case when the surgical site is imaged using wavelengths in the visible range where delicate structures are hidden by intervening tissue layers or are not salient relative to their surroundings. In some cases, the technology described herein may be particularly useful for new surgeons who may find it beneficial to be able to more easily distinguish the ureter from the surrounding fat layers.

Aspects of the technology are described primarily in terms of an implementation using a da Vinci® Surgical System, commercialized by Intuitive Surgical, Inc. of Sunnyvale, Calif. Examples of such surgical systems are the da Vinci® Xi™ Surgical System (Model IS4000) and the da Vinci® Si™ HD™ Surgical System (Model IS3000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

Figure 1A:
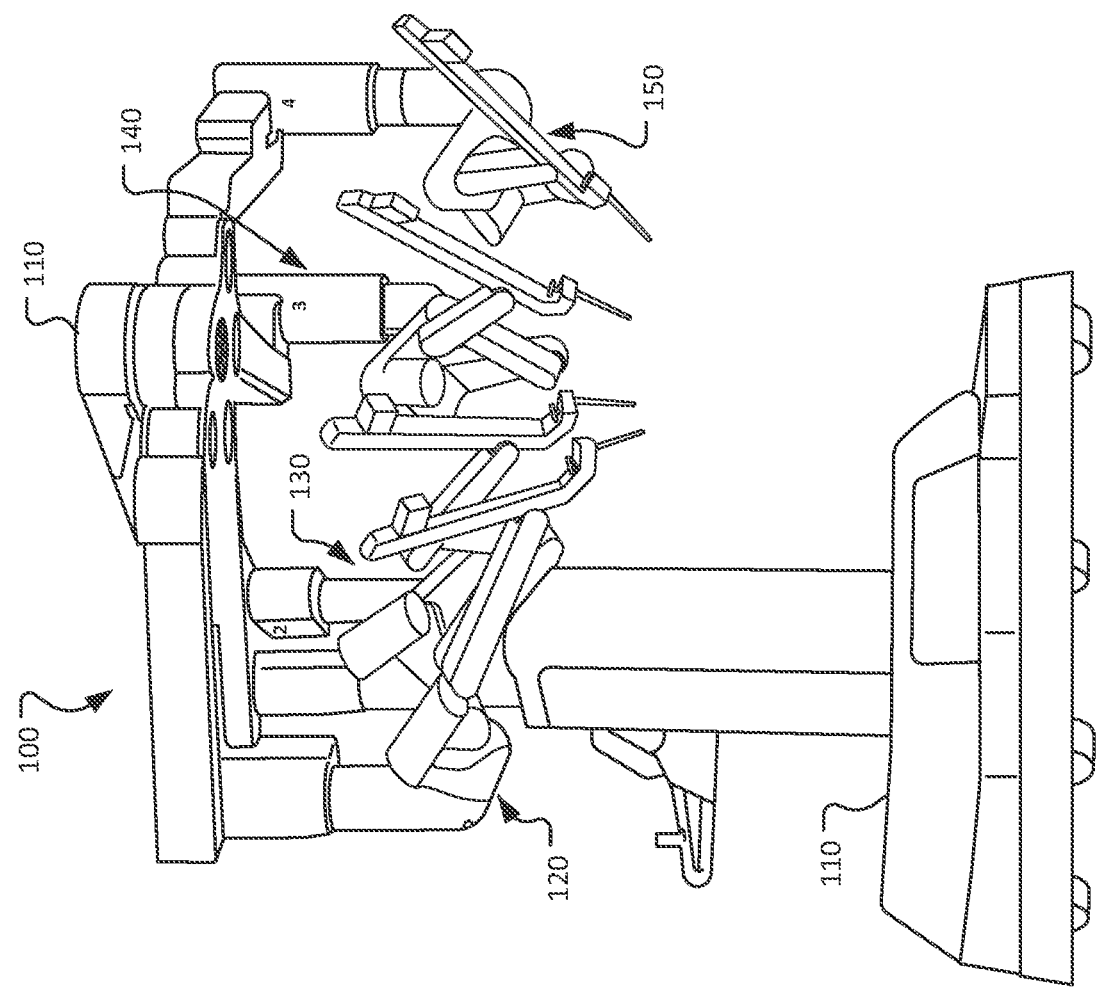
FIG. 1A is a perspective view of an example patient-side cart of a computer-assisted tele-operated surgery system.
Figure 1C:
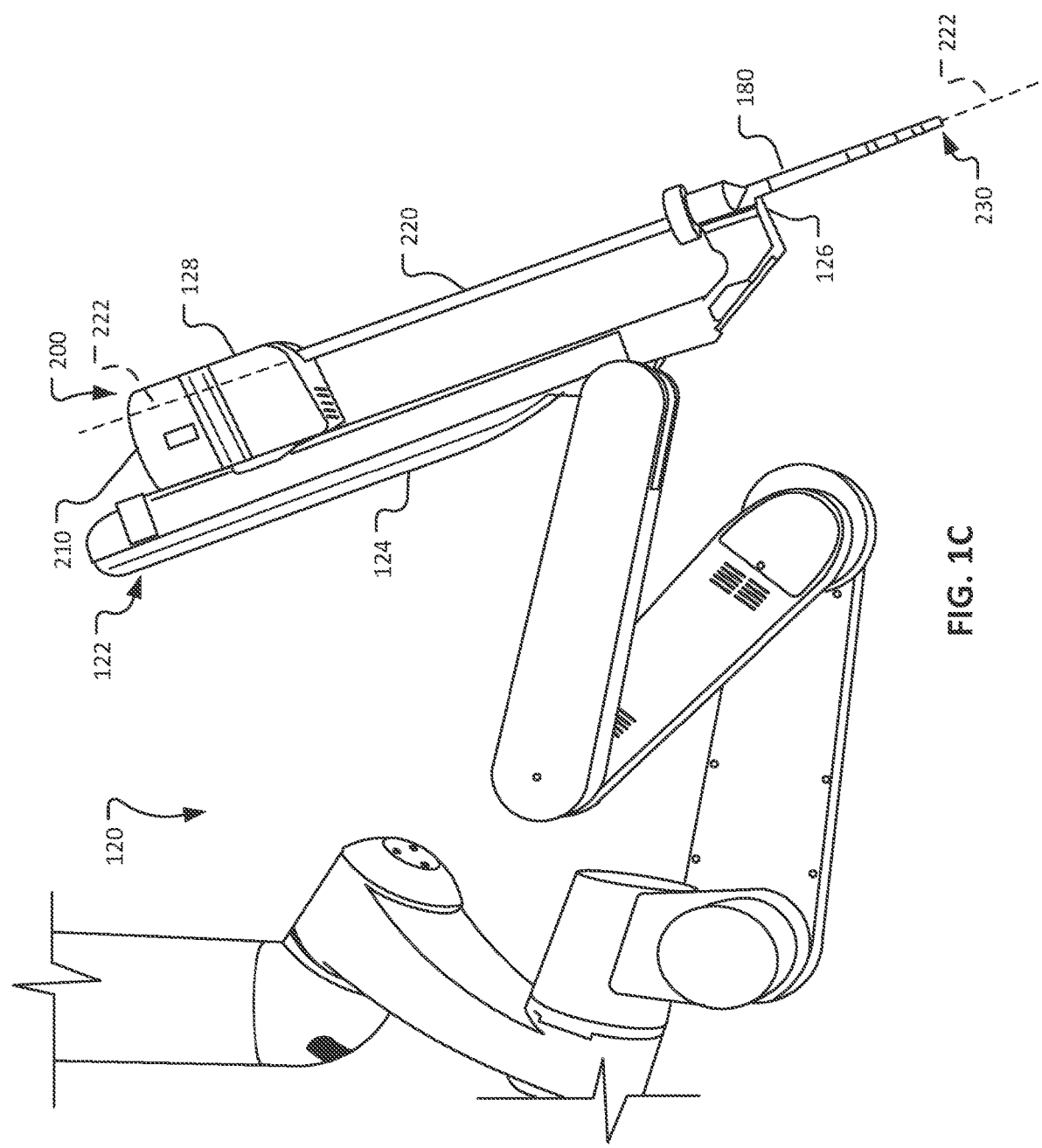

Referring to FIGS. 1A and 1B, systems for minimally invasive computer-assisted telesurgery (also referred to as MIS) can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment, the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the surgical site. Alternatively, the remaining robotic manipulator arm assembly may be used for introducing a second endoscope or another image-capturing device, such as an ultrasound probe, to the surgical site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices 49, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processing device 43 is provided in the surgeon console 40 for control and other purposes. The processing device 43 performs various functions in the medical robotic system. One function performed by processing device 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processing device 43 may also be distributed as subunits throughout the telesurgery system. One or more of the subunits may be physically remote (e.g., located on a remote server) to the telesurgery system.

Referring also to FIG. 10, the robotic manipulator arm assemblies 120, 130, 140, and 150 can manipulate devices such as surgical instruments to perform MIS. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43. The surgical instrument 200 includes a transmission assembly 210, the elongate shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 2:
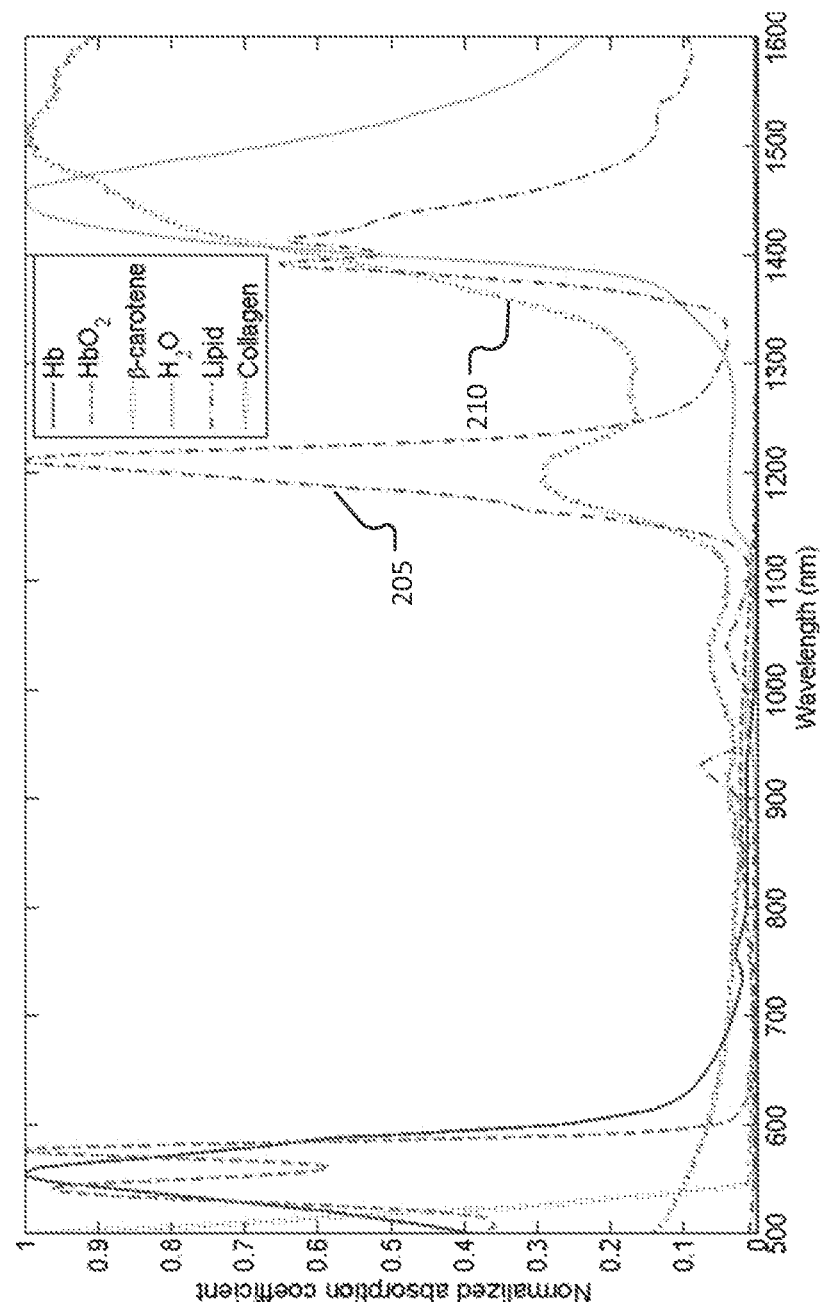
FIG. 2 is a collection of plots illustrating experimental results on absorption of electromagnetic radiation by different materials and tissues in a human body.

In some implementations, in order to enhance the visible differences between different tissues in the representations rendered on the surgeon's console 40, the illumination wavelengths wavelength ranges can be selected in accordance with the tissues being imaged. Light interacts with different tissues in different ways, for example, due to corresponding variations in absorption, reflection, and/or scattering of light. In some implementations, the illumination wavelengths or wavelength ranges can be selected, for example, based on experimental or theoretical knowledge about the absorption and/or reflection characteristics of the corresponding tissues being imaged. FIG. 2 is a collection of plots that illustrates experimental results on absorption of electromagnetic radiation by different materials and tissues in a human body. The x-axis of FIG. 2 represents wavelengths, and the y-axis represents normalized absorption coefficients. Therefore, FIG. 2 illustrates the variation in absorption characteristics of various components of a human body over the depicted range of wavelengths.

Figure 3B:
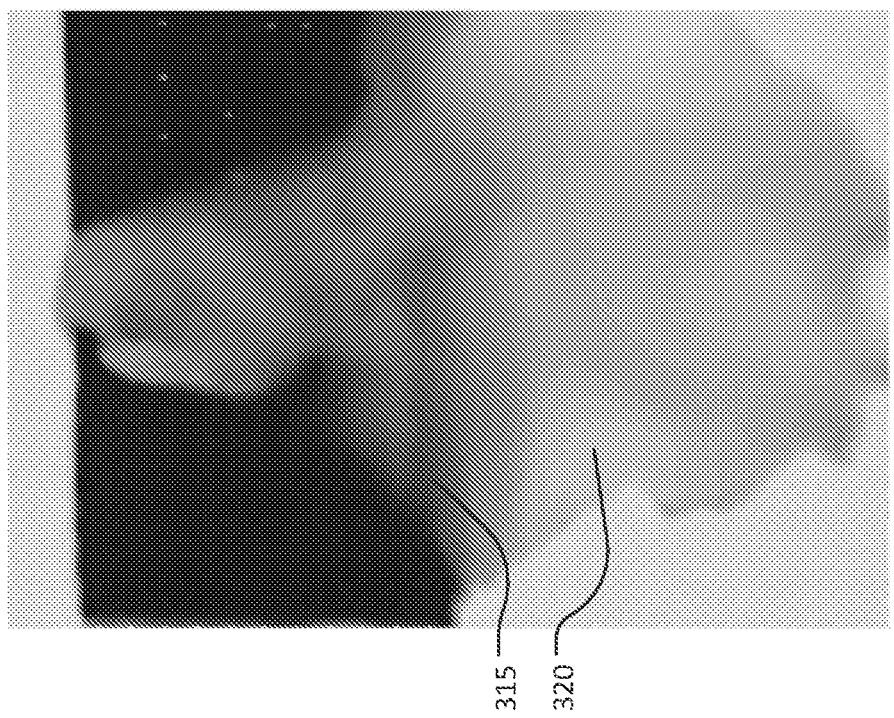
FIG. 3B shows the same portion of the human body, as in FIG. 3A, captured in a reduced-band image, in accordance with technology described herein.
Figure 3A:
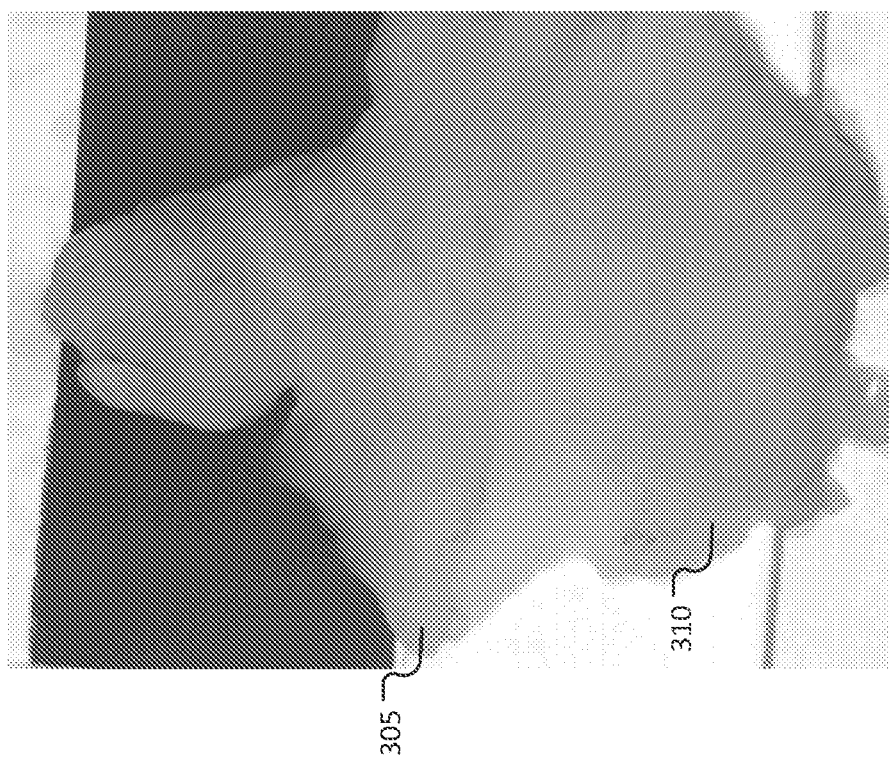
FIG. 3A shows a ureter in a human body in the presence of adjacent layers of fat, as captured in a broadband image.

From the experimental results depicted in FIG. 2, it can be observed that the absorption characteristics of some components are generally similar in the visible range or spectrum of wavelengths. For example, by comparing the plot 205 for lipid (fats) and the plot 210 for collagen (connective tissue), it can be observed that the normalized absorption coefficient for both remain generally low (around 0.1 or lower) at lower wavelengths until about 1100 nm. This range includes the upper end of about 700 nm of the visible spectrum. Therefore, imaging lipids and collagens using illumination in the visible spectrum results in similar absorption by the two types of tissues, which can sometimes make it challenging to distinguish them in the resulting image. An example of this is shown in FIG. 3A, which shows a ureter in a human body in the presence of adjacent and covering layers of fat, as captured in a typical broadband image obtained using wavelengths in the visible spectrum. The portion 305 represents the location of the ureter in the image, and the portion 310 represents the surrounding fat layers. However, because the characteristics in the visible spectrum are substantially similar for lipids and collagens, the boundary between the ureter and the fat layers may be quite subtle and hard to see.

The technology described herein can allow for selecting imaging wavelengths in the near-infrared (NIR) or infrared (IR) spectrum, such that the visible differences between different tissues (collagen and fat, in one example) can be enhanced in the presented images. In some implementations, this can be achieved by selecting particular wavelengths (or ranges of wavelengths) in the NIR and/or IR range (e.g., in the range of 850-2000 nm) in accordance with the tissues that are being imaged, and capturing images based on such wavelengths. For example, in order to enhance visible differences between collagen and lipid, the tissues can be imaged using a first wavelength range, at which the absorption of electromagnetic radiation by the collagen is significantly higher than that by the lipid (or, correspondingly, the amount of electromagnetic radiation reflected from or transmitted through collagen is lower than the corresponding amount for lipid), and using a second wavelength at which the absorption by the lipid is significantly higher than that by the collagen (or, correspondingly, the amount of electromagnetic radiation reflected from or transmitted through lipid is lower than the corresponding amount for collagen). In some implementations, such complementary absorption characteristics can cause the corresponding wavelengths to be absorbed by the tissues substantially differently, thereby enhancing the visible differences in the resulting image.

In some implementations, the particular wavelengths or wavelength ranges for imaging the different tissues can be selected based on experimental data. For example, referring to the plots 205 and 210 in FIG. 2, the absorption for lipid at around 1200 nm is seen to be significantly higher than that for collagen. In addition, the absorption for collagen at around 1350 nm is seen to be significantly higher than that for lipid. Therefore, the wavelength ranges 1200-1250 nm and 1300-1350 nm can be selected for enhancing the visible differences between a ureter and the adjacent fat layers. FIG. 3B shows the same portion of the human body, as in FIG. 3A, captured in a reduced-band image that uses the 1200-1250 nm and 1300-1350 nm wavelength ranges. In some implementation, instead of wavelength ranges, one or more discrete wavelengths may also be selected for imaging particular tissues. For example, 1200 nm and 1350 nm wavelengths may be selected to enhance visible difference between collagens and lipids in the resultant image. As seen from FIG. 3B, due to the different absorption characteristics of collagen and fat for the selected wavelengths, the NIR images may be presented to accentuate visibly the differences between the representation of the ureter 315 and the representation of the fat layers 320 in FIG. 3B are significantly enhanced in the visible image presented as compared to the differences between the corresponding portions 305 and 310, respectively, in FIG. 3A.

In some implementations, one or more additional wavelengths or wavelength ranges may also be selected for the imaging the different tissues. The additional wavelengths may be selected based on various criteria. In some implementations, a third wavelength or wavelength range may be selected to improve the overall image presented by using the third wavelength to estimate one or more characteristics of the surgical site. For example, the third wavelength or wavelength range can be selected such that the absorption or reflectance/transmission characteristics for that wavelength or wavelength range are substantially similar for the tissues being imaged. In that case, the reflectance associated with the third wavelength or wavelength range provides a local reference brightness that visibly enhances the differences between the tissues of interest. In some cases, this can be important from a human perception perspective, and potentially improve intelligibility of the rendered images for surgeons.

In some implementations, the third wavelength or wavelength range may also be selected to further improve the differentiability between the tissues. For example, in the case of imaging collagen and lipid, the third wavelength or wavelength range can be selected such that at the selected wavelength or wavelength range, the absorption of electromagnetic radiation by the collagen is significantly higher than that by the lipid, or correspondingly, the amount of electromagnetic radiation reflected from or transmitted through collagen is lower than the corresponding amount for lipid. A wavelength or wavelength range with the reverse characteristics may also be chosen. For example, the third wavelength or wavelength range can be selected such that at the selected wavelength or wavelength range, the absorption of electromagnetic radiation by the lipid is significantly higher than that by the collagen, or correspondingly, the amount of electromagnetic radiation reflected from or transmitted through lipid is lower than the corresponding amount for collagen.

In some implementation, the third wavelength or wavelength range is outside the visible range of wavelengths. In some implementations, the third wavelength or range of wavelengths is inside the visible range of wavelengths such that a combination of wavelengths in the visible and IR/NIR range is used for the overall imaging process. In some cases, this may improve the perceptibility or intelligibility of the images rendered on the surgeon's console. For example, by selecting a 600-700 nm range as the third wavelength range, and mapping the information obtained using the first and second wavelength ranges to appropriate portions of the visible range, at least some of the imaged tissues can be made to appear close to natural in color. In the example of collagen and lipids, by mapping the 1300-1350 nm wavelengths to a "green" portion of the visible range, mapping the 1200-1250 nm wavelengths to a "blue" portion of the visible range, and retaining the 600-700 nm in the original "red" portion of the visible range, the lipid portions can be made to appear more natural (without having to capture a normal color image with white illumination) as compared to the case where the mappings to the visible range are not performed. The above-described mapping may also make the blood vessels appear blue, which in some cases can help the surgeon to locate them more easily.

The imaging process using a selected set of wavelengths or wavelength ranges, as described above, may be implemented using various types of imaging systems. In some implementations, the camera sensors can include three separate sensors (e.g., charge-coupled devices (CCD)) or detectors, each configured to detect a particular wavelength or wavelength range. This can be achieved, for example, by using an appropriate filter configured to pass the appropriate wavelengths for a particular sensor. In some cases, a sensor itself may be sensitive to a particular range of wavelengths. For example, a complementary metal oxide semiconductor (CMOS) sensor can be used for wavelengths below 1000 nm, and an Indium Gallium Arsenide (InGaAs) sensor can be used for wavelengths above 1000 nm. Other types of imaging sensors may also be used.

When multiple types of sensors and/or filters are used, they can be arranged in different ways in sensor arrays of the camera. For example, two different types of sensors and/or filters can be arranged in a checkerboard pattern on the sensor array of the camera. When such bandwidth-limited sensors or filters are used, the surgical site may be illuminated using wideband illumination that causes the target tissues to reflect or transmit at the selected wavelengths or wavelength ranges. The reflected or transmitted electromagnetic radiation from the tissues can then be simultaneously collected by the multiple sensors as the representations of the multiple bandwidth-limited images.

In some implementations, the same sensor may be used for obtaining representations of the multiple bandwidth-limited images. For example, the surgical site may be sequentially illuminated using different wavelengths and the same sensor can be used to capture the electromagnetic radiation transmitted or reflected from the target tissues. The illumination wavelengths can be selected in accordance with the selected wavelengths for the target tissue types, as described above. Such narrowband illumination can be achieved, for example, using laser sources. Other implementations, including those that use a combination of the above-mentioned techniques, are also within the scope of this disclosure. In some implementations, where the illumination for tissue discrimination is outside the sensitivity of the image sensor used for normal white light imaging, the two light sources may be on simultaneously. If there is overlap in the sensitivities of the image sensors, then one or more filters may be incorporated if needed. In some implementations, these filters may be either reflective or absorbing.

Figure 4:
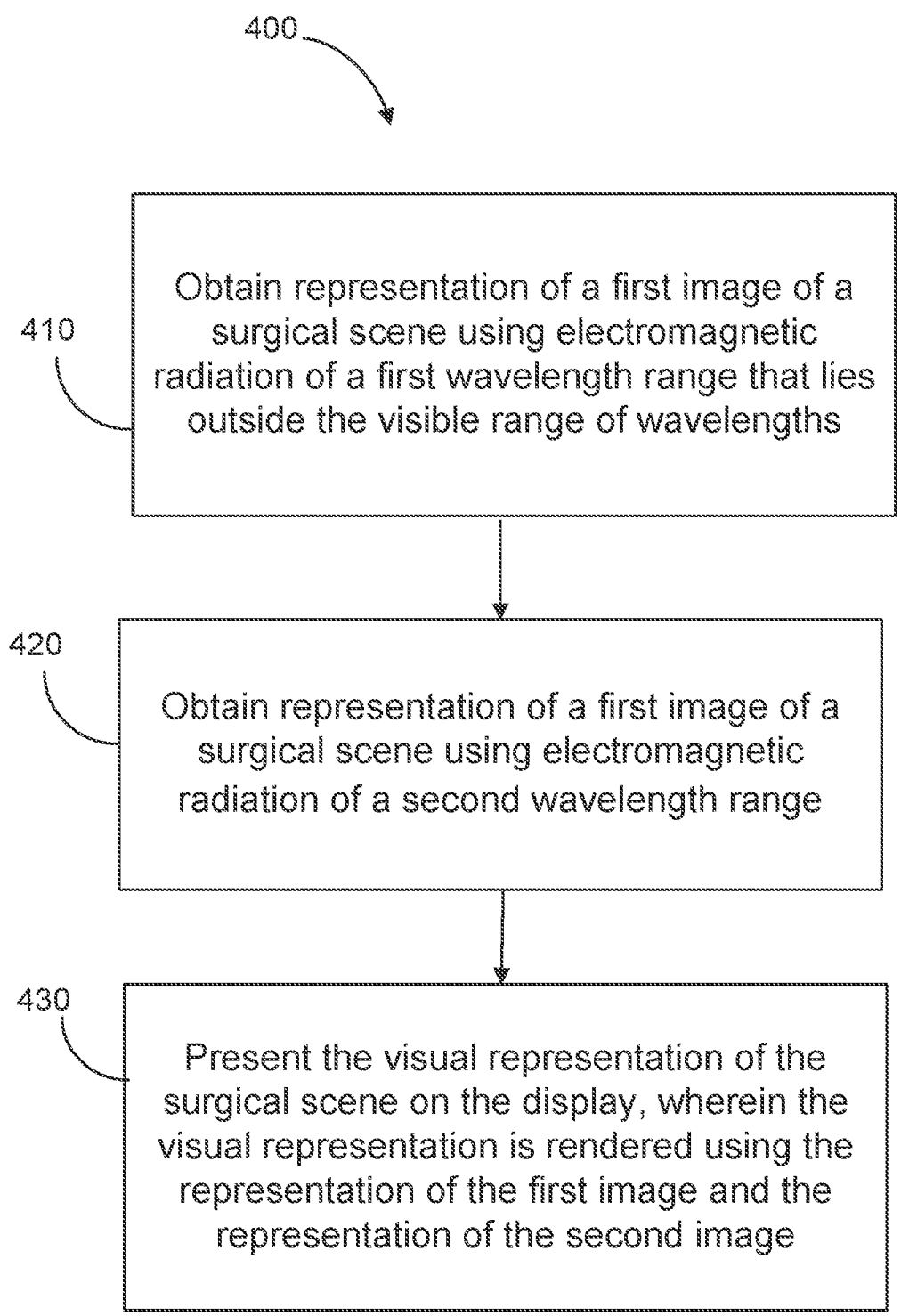
FIG. 4 is a flowchart illustrating an example process of providing visual feedback during a surgical process.

FIG. 4 is a flowchart illustrating an example process 400 of providing visual feedback during a surgical process using a visual representation of a surgical scene rendered on a display associated with a surgical device. In some implementations, at least a portion of the process 400 may be executed at a surgeon's console of a computer-assisted tele-operated surgery system (e.g., by the processing device 43 of the surgeon's console 40 depicted in FIG. 2). Operations of the process 400 include obtaining a representation of a first image of the surgical scene using electromagnetic radiation of a first wavelength range that lies outside the visible range of wavelengths (410). The first wavelength range (which in some cases may include one or more discrete wavelengths) can be selected such that an amount of electromagnetic radiation of the first wavelength range received from a first tissue type is lower than an amount of electromagnetic radiation of the first wavelength range received from a second tissue type. In some implementations, the first tissue type can be one of collagen, lipid, or muscle, and the second tissue type can be one that is different from the first tissue type. For example, the first tissue type can be collagen, and the second tissue type can be lipid, which allows for enhancing visible differences between a ureter and surrounding fat layers in an image of a corresponding surgical site, as rendered on a surgeon's console.

Operations of the process 400 also includes obtaining a representation of a second image of the surgical scene using electromagnetic radiation of a second wavelength range that lies outside the visible range of wavelengths (420 The second wavelength range (which in some cases may include one or more discrete wavelengths) can be selected such that an amount of electromagnetic radiation of the second wavelength range received from the second tissue type is substantially different than an amount of electromagnetic radiation of the second wavelength range received from the first tissue type. In some implementations, each of the first wavelength range and the second wavelength range are in the range 700-2000 nm. For example, the first wavelength range can be in the range 1300-1350 nm and the second wavelength range can be in the range 1200-1250 nm.

In some implementations, obtaining the representation of the first or second image of the surgical scene can include illuminating the surgical scene using electromagnetic radiation of the first wavelength or the second wavelength, and generating the representation of the first image or second image, respectively, using data captured by a sensor configured to sense portions of the electromagnetic radiation reflected or transmitted from the surgical scene. In some implementations, the illumination wavelengths can be selected such that portions of the illumination reflected or transmitted from the target tissues are in the corresponding selected wavelength ranges. In some implementations, illuminating the surgical scene using electromagnetic radiation can include illuminating the surgical scene using electromagnetic radiation of the first wavelength during a first time period, and illuminating the surgical scene using electromagnetic radiation of the second wavelength during a second time period. The second time period can be completely, or at least partially non-overlapping with the first time period.

In some implementations, obtaining the representation of the first or second image of the surgical scene can include illuminating the surgical scene using broadband electromagnetic radiation that includes multiple wavelengths, and generating the representations of the first and second images using data captured by a first sensor and a second sensor, respectively. In such cases, the first sensor can be configured to sense a first portion of the electromagnetic radiation reflected or transmitted from the surgical scene, and the second sensor can be configured to sense a second portion of the electromagnetic radiation reflected or transmitted from the surgical scene. The first portion of the electromagnetic radiation can be generated using a first filter configured to selectively pass electromagnetic radiation in the first wavelength range, and the second portion of the electromagnetic radiation can be generated using a second filter configured to selectively pass electromagnetic radiation in the second wavelength range.

In some implementations, a representation of a third image of the surgical scene can be obtained based on a third wavelength range (which may include one or more discrete wavelengths) that lies outside the visible range of wavelengths, and presenting a visual representation of the surgical scene on the display. The visual representation presented on the surgeon's console can be rendered also using the representation of the third image. The third wavelength or wavelength range may be selected based on various criteria. For example, the third wavelength or wavelength range may be selected, for example, to improve the overall reflectance in the resulting image, to further improve the differentiability between the tissues, and/or improve human-perceptibility of the final rendered image. In some implementations, the third wavelength range can be selected based on interaction of the different target tissues with electromagnetic radiation in the third wavelength range. For example, an absorption of electromagnetic radiation in the third wavelength range for one tissue type (e.g., lipid) can be substantially equal to (or significantly different from) an absorption of electromagnetic radiation in the third wavelength range for a different tissue type (e.g., collagen).

Operations of the process 400 can also include presenting the visual representation of the surgical scene on the display, wherein the visual representation is rendered using the representation of the first image and the representation of the second image (430). In some implementations, the representations of the first and second images may be processed in various ways to improve intelligibility and/or presentation of the visual representation. For example, the representations of the first and/or second images may be mapped on to other portions of the spectrum (e.g., within the visible range of the spectrum) to adjust the appearance of the visual representation. This may be done, for example, to influence the colors in which the different tissues are represented. In one particular example, by mapping a 1300-1350 nm range to the "green" portion of the visible spectrum, a 1200-1250 nm range to the "blue" portion of the visible spectrum, and selecting a third wavelength range in the "red" portion of the visible spectrum, the color of fat in the visual representation can be made to appear natural (or at least close to natural), and blood vessels can be made to appear blue. In some cases, the color mappings may be made in accordance with typical assumptions made by the surgeons about tissue types, and/or to improve surgeons' understanding of the visual representation. In some implementations, other forms of presentations may be used. For example, a small inset greyscale image can be presented in a picture-in-picture configuration, the greyscale image corresponding to the first or second images, or an image generated using some combination of information from the first and second images.

Other variations of the process described above are also possible. For example, the representation of the first image (corresponding to the first wavelength range) and the representation of the second image (corresponding to the second wavelength range) can be used in conjunction with a visible light image (obtained under substantially white light illumination) to present the visual representation of the surgical scene on the display. The first and second images, individually or in combination, can be used to modify the white light image to increase the visual saliency of particular tissue features. In some implementations, the capture of and use of the second image can be made optional, and only the first image may be used in conjunction with the visible light image in generating the visual representation. The white light image presents an image with particular features that are discriminated by the first and (optionally) second wavelength ranges.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Particular embodiments of the subject matter have been described. Other embodiments are within the scope of the following claims.

What is claimed is:

1. A method of providing visual feedback of a surgical process using a visual representation of a surgical scene rendered on one or more displays associated with a surgical device, the method comprising:
    obtaining a representation of a first image of the surgical scene using electromagnetic radiation of a first wavelength range that lies outside the visible range of wavelengths and lies within the near-infrared or infrared range of wavelengths, wherein an amount of electromagnetic radiation of the first wavelength range received by one or more sensors from a first tissue type is lower than an amount of electromagnetic radiation of the first wavelength range received for a second tissue type;
    obtaining a representation of a second image of the surgical scene using electromagnetic radiation of a second wavelength range that lies outside the visible range of wavelengths and lies within the near-infrared or infrared range of wavelengths, wherein an amount of electromagnetic radiation of the second wavelength range received by the one or more sensors from the second tissue type is substantially different than an amount of electromagnetic radiation of the second wavelength range received for the first tissue type; and
    presenting the visual representation of the surgical scene on the one or more displays, wherein the visual representation is rendered using the representation of the first image and the representation of the second image.

2. The method of claim 1, further comprising:
    receiving, via an input device, user-input for controlling at least a portion of the surgical device, wherein the user-input is received in response to presenting the visual representation.

3. The method of claim 1, wherein the first tissue type is collagen, and the second tissue type is lipid, and wherein the visual representation includes enhanced visible differences between a representation of a ureter and a representation of surrounding lipid layers.

4. The method of claim 1, wherein each of the first wavelength range and the second wavelength range are in the range of 700-2000 nm.

5. The method of claim 4, wherein the first wavelength range is 1300-1350 nm and the second wavelength range is 1200-1250 nm.

6. The method of claim 1, wherein obtaining the representation of the first or second image of the surgical scene using electromagnetic radiation of the first or second wavelength range, respectively, comprises:
outputting instructions to illuminate the surgical scene using electromagnetic radiation of the first wavelength range or the second wavelength range; and
generating the representation of the first image or second image, respectively, using data captured by the one or more sensors, wherein the one or more sensors are configured to sense portions of the electromagnetic radiation reflected or transmitted from the surgical scene.

7. The method of claim 6, wherein illuminating the surgical scene using electromagnetic radiation in the first wavelength range or the second wavelength range comprises:
illuminating the surgical scene using electromagnetic radiation in the first wavelength range during a first time period; and
illuminating the surgical scene using electromagnetic radiation in the second wavelength range during a second time period that is at least partially non-overlapping with the first time period.

8. The method of claim 1, wherein obtaining the representation of the first or second image of the surgical scene using electromagnetic radiation in the first or second wavelength ranges, respectively, comprises:
illuminating the surgical scene using broadband electromagnetic radiation that includes multiple wavelengths;
generating the representation of the first image using data captured by a first sensor configured to sense a first portion of the electromagnetic radiation reflected or transmitted from the surgical scene, wherein the first portion of the electromagnetic radiation passes through a first filter configured to selectively pass electromagnetic radiation in the first wavelength range; and
generating the representation of the second image using data captured by the first sensor or a second sensor configured to sense a second portion of the electromagnetic radiation reflected or transmitted from the surgical scene, wherein the second portion of the electromagnetic radiation passes through a second filter configured to selectively pass electromagnetic radiation in the second wavelength range.

9. The method of claim 1, wherein obtaining the representation of the first or second image of the surgical scene using electromagnetic radiation in the first or second wavelength ranges, respectively, comprises:
illuminating the surgical scene using broadband electromagnetic radiation that includes multiple wavelengths;
generating the representation of the first image using data captured by a first sensor configured to selectively sense a first portion of the electromagnetic radiation in the first wavelength range, as reflected or transmitted from the surgical scene; and
generating the representation of the second image using data captured by the first sensor or a second sensor configured to selectively sense a second portion of the electromagnetic radiation in the second wavelength range as reflected or transmitted from the surgical scene.

10. The method of claim 1, further comprising:
obtaining a representation of a third image of the surgical scene based on a third wavelength range that lies outside the visible range of wavelengths; and
presenting the visual representation of the surgical scene on the one or more displays, wherein the visual representation is rendered also using the representation of the third image.

11. The method of claim 10, wherein the third wavelength range is selected such that an absorption of electromagnetic radiation in the third wavelength range for lipid is substantially equal to an absorption of electromagnetic radiation in the third wavelength range for collagen.

12. The method of claim 10, wherein the third wavelength range is selected such that an absorption of electromagnetic radiation in the third wavelength range for lipid is substantially different from an absorption of electromagnetic radiation in the third wavelength range for collagen.

13. A surgical system comprising:
one or more display devices;
one or more sensors configured to receive electromagnetic radiation reflected or transmitted from a surgical scene; and
one or more processing devices configured to perform operations comprising:
obtaining a representation of a first image of the surgical scene using electromagnetic radiation of a first wavelength range that lies outside the visible range of wavelengths and lies within the near-infrared or infrared range of wavelengths, wherein an amount of electromagnetic radiation of the first wavelength range received by one or more sensors from a first tissue type is lower than an amount of electromagnetic radiation of the first wavelength range received for a second tissue type;
obtaining a representation of a second image of the surgical scene using electromagnetic radiation of a second wavelength range that lies outside the visible range of wavelengths and lies within the near-infrared or infrared range of wavelengths, wherein an amount of electromagnetic radiation of the second wavelength range received by the one or more sensors from the second tissue type is substantially different than an amount of electromagnetic radiation of the second wavelength range received for the first tissue type; and
presenting a visual representation of the surgical scene on the one or more display devices, wherein the visual representation is rendered using the representation of the first image and the representation of the second image.

14. The surgical system of claim 13, further comprising:
an input device configured to receive a user-input for controlling at least a portion of a surgical device, wherein the user-input is received in response to presenting the visual representation.

15. The surgical system of claim 13, wherein the first tissue type is collagen, and the second tissue type is lipid, and wherein the visual representation includes enhanced visible differences between a representation of a ureter and a representation of surrounding lipid layers.

16. The surgical system of claim 13, wherein each of the first wavelength range and the second wavelength range are in the range of 700-2000 nm.

17. The surgical system of claim 16, wherein the first wavelength range is 1300-1350 nm and the second wavelength range is 1200-1250 nm.

18. The surgical system of claim 13, wherein obtaining the representation of the first or second image of the surgical scene using electromagnetic radiation of the first or second wavelength range, respectively, comprises:
- illuminating the surgical scene using electromagnetic radiation of the first wavelength range or the second wavelength range; and
- generating the representation of the first image or second image, respectively, using data captured by the one or more sensors.

19. The surgical system of claim 18, wherein illuminating the surgical scene using electromagnetic radiation in the first wavelength range or the second wavelength range comprises:
- illuminating the surgical scene using electromagnetic radiation in the first wavelength range during a first time period; and
- illuminating the surgical scene using electromagnetic radiation in the second wavelength range during a second time period that is at least partially non-overlapping with the first time period.

20. One or more machine-readable non-transitory storage devices encoded with machine-readable instructions configured to cause one or more processing devices to perform operations comprising:
- obtaining a representation of a first image of a surgical scene using electromagnetic radiation of a first wavelength range that lies outside the visible range of wavelengths and lies within the near-infrared or infrared range of wavelengths, wherein an amount of electromagnetic radiation of the first wavelength range received by one or more sensors from a first tissue type is lower than an amount of electromagnetic radiation of the first wavelength range received for a second tissue type;
- obtaining a representation of a second image of the surgical scene using electromagnetic radiation of a second wavelength range that lies outside the visible range of wavelengths and lies within the near-infrared or infrared range of wavelengths, wherein an amount of electromagnetic radiation of the second wavelength range received by the one or more sensors from the second tissue type is substantially different than an amount of electromagnetic radiation of the second wavelength range received for the first tissue type; and
- presenting a visual representation of the surgical scene on one or more displays, wherein the visual representation is rendered using the representation of the first image and the representation of the second image.

* * * * *